(12) United States Patent
Lee et al.

(10) Patent No.: US 7,776,356 B2
(45) Date of Patent: Aug. 17, 2010

(54) MEMBRANE DEVICES WITH ELASTIC ENERGY BARRIERS

(75) Inventors: Sin-Doo Lee, Seoul (KR); Tae-Young Yoon, Gwacheon-si (KR); Cherl-Hyun Jeong, Seoul (KR); Sang-Wook Lee, Boryeong-si (KR)

(73) Assignees: Samsung SDI Co., Ltd., Gongse-dong, Giheung-gu, Yongin-si, Gyeonggi-do (KR); Seoul National University Industry Foundation, Bongchun-dong, Gwanak-gu, Seoul (KR)

( * ) Notice: Subject to any disclaimer, the term of this patent is extended or adjusted under 35 U.S.C. 154(b) by 387 days.

(21) Appl. No.: 11/727,354

(22) Filed: Mar. 26, 2007

(65) Prior Publication Data

US 2008/0033190 A1 Feb. 7, 2008

(30) Foreign Application Priority Data

Aug. 4, 2006 (KR) ...................... 10-2006-0073667

(51) Int. Cl.
*A61K 9/127* (2006.01)
*C12M 3/00* (2006.01)

(52) U.S. Cl. ..................................... 424/450; 435/287.9
(58) Field of Classification Search ........................ None
See application file for complete search history.

(56) References Cited

U.S. PATENT DOCUMENTS

2005/0009171 A1* 1/2005 Fertig et al. ............... 435/287.2
2005/0079507 A1* 4/2005 Fang ............................. 435/6

FOREIGN PATENT DOCUMENTS

WO 8600238 1/1986
WO 2006/068619 A1 6/2006

OTHER PUBLICATIONS

Groves et al.,"Micropatterning Fluid Lipid Bilayers on Solid Supports", Science 275: 651-653 (1997).*
C. Dietrich et al., "Lipid Rafts Reconsituted in Model Membranes", Biophysical Journal, vol. 80, pp. 1417-1428, Mar. 2001.
Kai Simons et al., "Lipid Rafts and Signal Transduction", Nature Reviews, vol. 1, pp. 31-41, Oct. 2000.
Deborah A. Brown et al., "Structure and Function of Sphingolipid- and Cholesterol-rich Membrane Rafts", The Journal of Biological Chemistry, vol. 275, No. 23, pp. 17221-17224, Jun. 9, 2000.
Joanna M. Cordy et al., "Exclusively targeting {beta}-secretase to lipid rafts by GPI-anchor addition up-regulates {beta}-site processing of the amyloid precursor protein", PNAS, vol. 100, No. 20, pp. 11735-11740, Sep. 30, 2003.
Cherlhyun Jeong et al., "Patterning Process of Membrane-Associated Proteins on a Solid Support with Geometrical Grooves", Mol. Cryst. Liq. Cryst., vol. 434, pp. 297-303, 2005.
Tae-Young Yoon et al., "Topographic control of lipid-raft reconstitution in model membranes", Nature Materials, vol. 5, pp. 281-285, Apr. 2006.
Tae-Young Yoon et al., "Spontaneous aggregation of lipids in supported membranes with geometrical barriers", Applied Surface Science 238, pp. 299-303, 2004.
E. Sackmann, "Supported Membranes: Scientific and Practical Applications", Science, 271, 5245, pp. 43-48, Jan. 5, 1996.
Richard G. W. Anderson et al., "A Role for Lipid Shells in Targeting Proteins to Caveolae, Rafts, and Other Lipid Domains", Science, vol. 296, pp. 1821-1825, Jun. 7, 2002.
Jeffrey T. Buboltz et al., "A novel strategy for the preparation of liposomes: rapid solvent exchange", Biochimica et Biophysica Acta 1417, pp. 232-245, 1999.
Don-A Ilbo, No. 26336, A26, Mar. 27, 2006 along with an English translation.
Hankyoreh 21, vol. 604, p. 87, Apr. 2006 along with an English translation.
Comparisons of detergent extraction and confocal microscopy. Biophys, J. 89. 1102-1108 2005 (cited in [0011] on p. 5).
Arun Radhakrichnan and Harden McConnell, Condensed complexes in vesicles containing cholesterol and phospholipids, PNAS 102, 12662-12666 2005 (cited in [0050]on p. 12).
Byron D. Gates and George M. Whitesides, Replication of vertical features smaller than 2nm by soft lithography, J. Am. Chem. Soc. 125, 14986-14987 2003 (cited in [0052] on p. 12-13).
J. Marra and J. Israelachvili, Direct Measurements of Forces between Phosphatidylcholine and Phosphatidylethanolamine Layers in Aqueous Electrolyte Solutions, Biochemistry, 24, 4608-4618 1985 (cited in [0052] on p. 13).

(Continued)

*Primary Examiner*—Anand U Desai
(74) *Attorney, Agent, or Firm*—Robert E. Bushnell, Esq.

(57) ABSTRACT

The present invention relates to a method for controlling the growth, size, and distribution of a lipid domain in a lipid layer using a substrate on which a topographic structure is formed, and a method of preparing a membrane device including a lipid layer having a lipid domain, where the growth, size, and distribution of the lipid domain can be controlled by said method, and a membrane device prepared thereby.

25 Claims, 14 Drawing Sheets

OTHER PUBLICATIONS

L.K. Tamm and H.M. McConnell, Supported phospholipid layers, Biophys, J., 47, 105-113 1985 (cited in [0052] on p. 13).

W.M. Choi and O.O. Park, Soft-imprint technique for multilevel microstructures using poly(dimethylsiloxane) mold combine with a screen mask, Appl. Phys. Lett., 85, 3310-3312 2004 (cited in [0053] on p. 13).

D. Braun and P. Fromherz, Fluorescence Interferometry of Neuronal Cell Adhesion on Microstructured Silicon, Phys. Rev. Lett., 81, 5241-5244 1996 (cited in [0053] on p. 13).

Y.Zhao, C.C.Lim, D.B. Sawyer, R.Liao, X.Zhang, Microchip for subcellular mechanics study in living cells, Sensors and Actuators B, 114, 1108-1115 2006 (cited in [0053] on p. 14).

Y. Fu and N.K.A. Bryan, Fabrication and characterization of slanted nanopillars array, J. Vac. Sci. Technol. B., 23, 984-989 2005 (cited in [0053] on p. 14).

H.K. Taylor of al., Characterizing and Predicting Spatial Non-uniformity in the Deep Reactive Ion Etching of Silicon. j. Electrochem. Soc. 153, C575 2006 (cited in [0055] on p. 14).

M.S. Chen et al., Structure of thin SiO2 films grown on Mo 112, Phys. Rev. B 69, 155404 2004 (cited in [0055] on p. 14).

Jennifer S. Hovis et al., patterning barriers to lateral diffusion in supported lipids layer membranes by blotting and stamping. Langmuir 16, 894-987 2000 (cited in [0055] on p. 14).

Papahadjopoulos and Miller, Biochem. Biophys. Acta., 135, 624-638 1967 (cited in [0046] on p. 20).

Cooper, M.A. Advances in Membrane Receptor Screening and Analysis, J. Mol. Recognit. 17, 286 2004 (cited in [0065] on p. 20).

Sackmann, E. Supported Membranes: Scientific and Practical Applications, Science, 271, 5245 1996 (cited in [0064] on p. 20).

Charitat, T. et al., Eur. Phys. J.B. 8, 583 1999 (cited in [0064] on p. 20).

Braun, D. & Fromherz, P. Fluorescence interferometry of neuronal cell adhesion on microstructured silicon, Phys. Rev. Lett. 81, 5241-5244 (1998) (cited in [0073] on p. 23).

* cited by examiner

MEMBRANE DEVICES WITH ELASTIC ENERGY BARRIERS

CROSS-REFERENCE TO RELATED APPLICATION AND CLAIM OF PRIORITY

This application claims priority to and the benefit of Korean Patent Application No. 10-2006-0073667 filed in the Korean Intellectual Property Office on Aug. 4, 2006, the entire content of which is incorporated herein by reference.

BACKGROUND OF THE INVENTION (a) Field of the Invention

The present invention relates to a method of controlling the growth, size, and distribution of a lipid domain in a lipid layer using a substrate on which a topographic structure is formed, and a method of preparing a membrane device including a lipid layer having a lipid domain, where the growth, size, and distribution of the lipid domain can be controlled by said method, and a membrane device prepared thereby.

(b) Description of the Related Art

Recently, researches in the field of biotechnology in the post genome era have been concentrated on the study of proteins, which are known to regulate most of the biological processes in cells, in order to delineate the function of genes that encode the proteins and have been discovered through various studies including the Human Genome Project. However, the protein studies are partly hampered by the fact that the deduction of protein functions directly from the nucleotide sequences encoding them is limited, and more importantly, proteins need to adopt a correct tertiary and/or quaternary conformation for reliable studies, which is known to be difficult to provide in vitro. It is the tertiary structure of proteins, which mature proteins should adopt in cells through a process called "protein-folding" under various physiological conditions, not the primary structure of proteins, i.e., amino acid sequences, that is critical for proper functional studies of proteins. The importance of the tertiary structures are manifested by the development of a disease caused by a malfunctioned protein due to its abnormal tertiary conformation, which is usually caused by a genetic defect or other external factors.

Proteins implicated in the development of diseases have become an important target for the development of novel therapeutic agents, as well as being the basis for studies to understand disease-causing mechanisms.

The majority of proteins conventionally studied in relation to the development of a disease belong to a class of protein called a water-soluble protein. Among them are proteases, phosphatases, and kinases that are known to regulate the function of proteins by modulating a degradation, synthesis, and/or phosphorylation thereof. However, there are many other proteins that are also known to be involved in causing a disease and belong to another class of protein called a membrane protein, which is located in cell membranes and the study of which is less progressed than the study of water-soluble proteins. This is partly because membrane proteins are not amenable to isolation in a pure form, which is often a prerequisite for the study thereof. This is in contrast to water-soluble proteins, which are relatively easy to synthesize and purify in large quantities from prokaryotic and eukaryotic cells using the well established methods known in the art. In addition, water-soluble proteins usually do not require special environments/experimental settings for analysis, such as a cellular structure, e.g. cell membranes, whereas membrane proteins need to be in the context of cell membranes for their proper function and analysis. All of these combined make water-soluble proteins a more attractive target for research. For example, three-dimensional structures have been identified for more than 20,000 water-soluble proteins, whereas only around 20 membrane proteins have been identified at the three dimensional level. This clearly shows the difficulty associated with the study of membrane proteins.

The difficulty associated with the production, purification, and study of membrane proteins mainly stems from their structures and location in cells. The membrane proteins largely comprised of two parts; a hydrophilic part that is present outside of the lipid layer of a cell membrane and a hydrophobic part that is embedded within the lipid layer. Accordingly, in order for the functional study of membrane proteins to be possible, experimental settings that may accurately reconstitute cell membranes as found in vivo are required. The experimental settings would also be able to provide an environment where hydrophilic and hydrophobic regions coexist and thus allows a formation of the proper tertiary structure of membrane proteins.

However, it is very difficult to reproduce such an environment in vitro where membrane proteins would be able to adopt a proper tertiary and/or quaternary structure and interact with other proteins in the membrane as they would do in vivo. Previous efforts to provide such an environment include the use of a cell membrane prepared by isolating the membrane components of cells employing a variety of surfactants but they did not bring satisfactory results [C. Dietrich, et al., Lipid raft reconstituted in model membranes, Biophys. J. 80, 1417-1428 2001].

This is partly explained by a recently developed theory called "the lipid-raft model", in which signaling membrane molecules are thought to be compartmentalized rather than continuously drifted in cell membranes as suggested by the previous, widely accepted theory called "the fluid mosaic model". The lipid-raft model has given a new insight into how the lipids and membrane proteins in cell membranes are distributed and had a profound impact on the structure and functional studies of membrane proteins. According to the fluid mosaic model, membrane proteins are considered continuously drifted in cell membranes having a lipid bi-layer structure, resulting in a random and uniform distribution of the components within cell membranes. According to the lipid-raft model, however, which is being increasingly supported by accumulating data from many studies, membrane proteins show a localized distribution within cell membranes, being located on a defined area of the cell membranes called a lipid domain, such as a lipid raft, where they specifically interact with other molecules to exert functions [Simons, K and Toomre, D. Lipid rafts and signal transduction, Nat. Rev. Mol. Cell Biol. 1, 31-41 2000; Brown, D. A. and London, E. Structure and function of sphingolipid- and cholesterol-rich membrane rafts, J. Biol. Chem. 275, 17221-17224 2000].

Accordingly, considering that membrane proteins play a crucial role in various aspect of cell function, it is clear that a lipid domain including a lipid raft as suggested by the lipid-raft model would also play an important role for cellular functions, for example, intercellular communication, signal transductions, polarity of cells, cell fusion, and transport across cell membranes such as ion transfer. In support of this, recently, lipid raft domains are found closely involved in the development of human diseases such as senile dementia caused by the accumulation of amyloid beta, and bovine spongiform encephalopathy caused by the accumulation of a prion protein [Joanna M. Cordy, Ishrut Hussain, et al., Exclusively targeting-secretase to lipid rafts by GPI-anchor addition up-regulates-site processing of the amyloid precursor protein, PNAS 100, 11735-11740 2003].

Therefore, there is an urgent need for the development of an in vitro cell membrane model system that would be able to reconstitute and regulate the lipid domains in vitro in a way similar to those found in vivo and thus provide an environment that allows membrane proteins to function in vitro as they do in vivo. This will greatly enhance our understanding of membrane proteins as well as their interactions with other proteins or components, leading to the development of new therapeutic agents. Such a system would also require a precise control of the growth, size, and spatial distribution of the lipid domain including a lipid raft, enabling a more systematic large-scale in vitro study of the lipid-raft model. However, no such systems are developed in the art.

The conventional methods to analyze lipid domains are limited and usually considered very destructive, and include treating cells with harsh reagents such as Trition X-100 and extracting whole cell membranes followed by isolation of the lipid domains, discarding the rest of the membrane components [Comparisons of detergent extraction and confocal microscopy, Biophys. J. 89, 1102-1108 2005]. Furthermore the conventional methods do not provide any control over the selectivity for lipid domains and the spatial distribution and size of lipid domains including lipid rafts in the context of cell membranes.

SUMMARY OF THE INVENTION

An improvement method for preparing a membrane device and an improvement membrane device are provided.

An improved method for controlling a formation of a lipid domain in a lipid layer on a substrate is provided.

Embodiments of the present invention provide a method for controlling the growth, size, and distribution of a lipid domain in a lipid layer in a micrometer scale without disrupting the two dimensional fluidity of the lipid layer, by using a substrate on which topographic structure is formed, a method for preparing a biomembrane device including a lipid layer having a lipid domain that can be controlled by said method, and an in vitro biomembrane system prepared thereby, which reconstitutes the in vivo cell membrane in vitro.

In one aspect, the present invention provides a method for preparing a biomembrane device, including (i) providing a topographic structure on a substrate, and (ii) providing a lipid layer having a lipid domain on the topographic structure of the substrate, wherein the growth, size, and distribution of the lipid domain are controlled by the topographic structure.

In another aspect, the present invention provides a method for controlling the growth, size, and distribution of a lipid domain in a lipid layer on a substrate, wherein the growth, size, and distribution of the lipid domain are controlled by use of a substrate on which a topographic structure is provided.

In yet another aspect, the present invention provides a method for controlling a formation of a lipid domain in a lipid layer on a substrate, including using at least two topographic structures formed on the substrate to control a growth, a size and a distribution of the lipid domain.

The use of at least two topographic structures may include forming at least two of (i) a topographic wall prohibiting the distribution of the lipid domain, (ii) a smooth region promoting the growth of the lipid domain, and (iii) a corrugated region prohibiting the growth of the lipid domain to control the formation of the lipid domain.

In another aspect, the present invention provides a biomembrane device including a substrate having a topographic structure on the surface of the substrate, a lipid layer including a lipid domain provided on the substrate, wherein the topographic structure generates a free energy difference within the lipid layer, whereby the growth, size, and distribution of the lipid domain are controlled.

In one embodiment of said methods and device, the topographic structure of the substrate includes at least one structure selected from the group consisting of a topographic wall, a smooth region, and a corrugated region.

In another embodiment of said methods and device, the topographic structure of the substrate includes a smooth region and a corrugated region.

In yet another embodiment of said methods and device, the topographic structure of the substrate includes a smooth region, a corrugated region, and a topographic wall formed at the interface between the smooth region and the corrugated region.

In yet another embodiment of said methods and device, the corrugated region prohibits the growth of a lipid domain, the smooth region promotes the growth of a lipid domain, and the topographic wall prevents the distribution of a lipid domain.

In yet another embodiment of said methods and device, the control of the growth and distribution of a lipid domain includes a drift of a lipid domain, a growth of a lipid domain at a predefined area, a localized distribution of a lipid domain, and a spatial confinement of a lipid domain in a lipid layer.

In yet another embodiment of said methods and device, the lipid layer is in a lipid bi-layer.

In yet a further embodiment of said methods, the topographic structure of step (i) is formed by at least one process selected from the group consisting of etching, stamping, photo-irradiation, and deposition.

In yet a further embodiment of said methods, the lipid layer of step (ii) is provided by at least one process selected from the group consisting of (i) rupture and fusion of a vesicle on the substrate, (ii) fixation of a vesicle onto the substrate by using a hydrophilic linker or a receptor with a biotinyl attached thereto, (iii) fixation of whole lipid extracted from cells onto the substrate by using a hydrophilic linker or a receptor with a biotinyl attached thereto, and (iv) incorporating a lipid mono-layer formed on a water-air interface onto the substrate.

In yet a further embodiment of said methods and device, the substrate is prepared by using material selected from the group consisting of mica, graphite, silicon dioxide, polydimethylsiloxane, silicone, glass, and plastic.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION OF THE INVENTION

The term "topographic structure" used herein indicates a topographic surface modification of a substrate.

The term "a lipid domain" used herein indicates a cholesterol- and sphingolipid-rich domain in a lipid layer, which is usually formed through a close packing of the lipids such as sphingomyelin with a long and straight hydrocarbon chain and sterol units (e.g., cholesterol).

The term, "lipid layer" as used herein encompasses both a lipid mono-layer and a lipid bilayer, and thus refers to a monolayer or bilayer of lipid molecules, for example, phospholipids, in which the lipid molecules comprised of a hydrophobic hydrocarbon chain (e.g., fatty acids) called a tail, and a hydrophilic head (e.g., phosphate), which adopt a highly ordered structure, with the tails facing each other toward the center of the layer.

Figure 1:
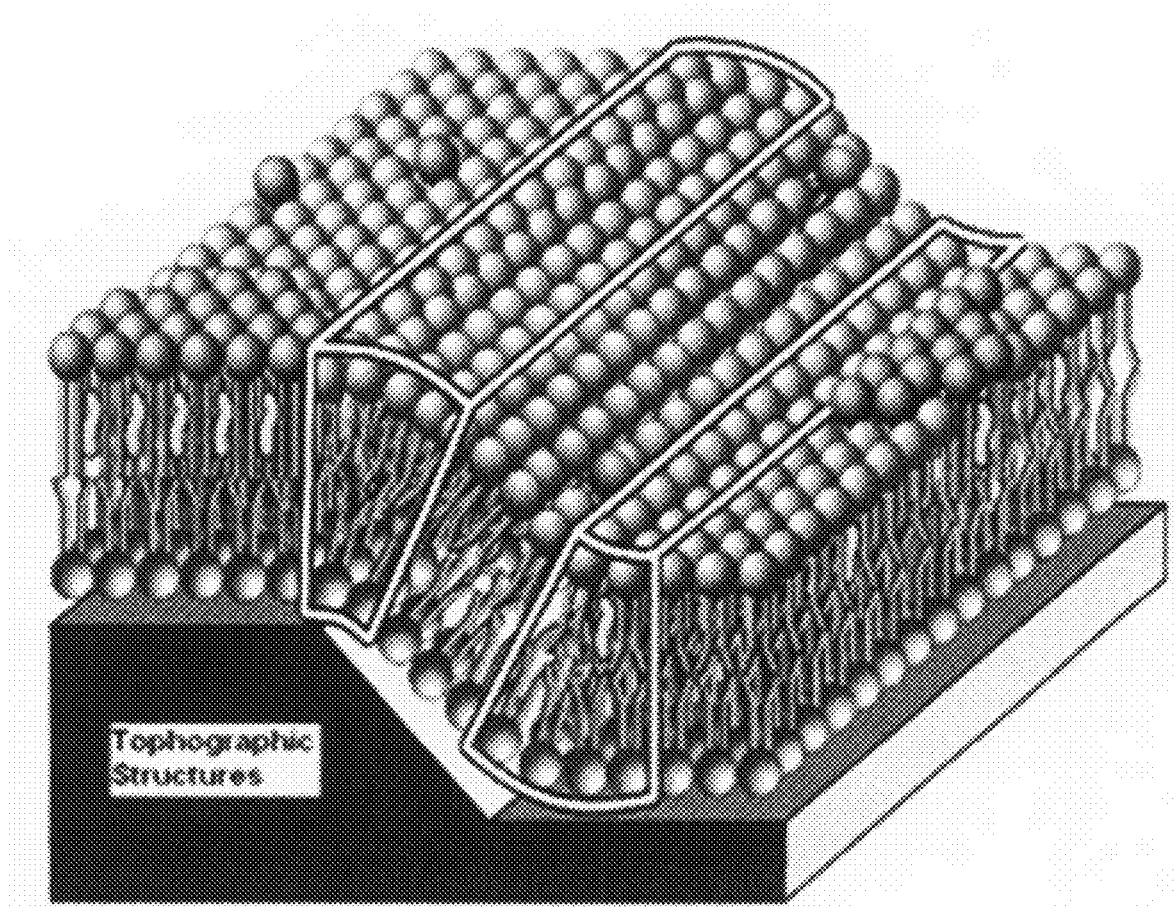
FIG. 1 is a schematic view showing one topographic structure formed on a substrate, the structure being a topographic wall that produces elastic energy barriers at two edges (the white lines) resulting from elastic distortions of a lipid layer, which then prevent the distribution of lipid domains.

The present inventors unexpectedly discovered that substrates on which a topographic structure is formed can be used to control the growth, size, and distribution of a lipid domain (for example, a lipid raft) in a lipid layer in a supported membrane system simulating a biological membrane. A lipid layer resting on the topographic structure closely follows the curvature surface of the topographic structure due to its innate two dimensional fluidity, and the topographic structure causes elastic distortions of the lipid layer. For example, as shown in FIG. 1, a topographic wall integrated with the substrate generates elastic distortions (the white lines) of the lipid layer at the two edges of the topographic wall. Accordingly, by employing topographic modification of the surface of the substrate having one or more particular shapes, it was found that the growth, size, and distribution of the lipid domain, such as lipid rafts, can be precisely controlled.

In one aspect, the present invention provides a method for preparing a biomembrane device including the steps of (i) providing a topographic structure on a substrate, and (ii) providing a lipid layer having a lipid domain on the topographic structure of the substrate, wherein the growth, size, and distribution of the lipid domain are controlled by the topographic structure.

The term "a lipid domain" used herein indicates a cholesterol- and sphingolipid-rich domain in a lipid layer, which is usually formed through a close packing of the lipids such as sphingomyelin with a long and straight hydrocarbon chain and sterol units (e.g., cholesterol). The lipid domain according to the embodiments of the present invention includes, but is not limited to, caveolae, lipid raft domain, and those disclosed in R. G. W. Anderson and K. Jacobson, A Role for Lipid Shells in Targeting Proteins to Cavelolae, Rafts and other Lipid Domains, Science, 296, 1821-1825 2002, which is incorporated herein by reference. In one embodiment of the present invention, the lipid domain is a lipid raft. The lipid domain contains highly ordered hydrocarbon chains compared to other regions in the lipid layer. The high degree of chain order provides an environment suitable for interaction with membrane proteins. As a result, membrane proteins are confined within a lipid domain once they reach the lipid domain through a lateral movement in a membrane. Thus, the lipid domains are rich in membrane proteins compared to other parts of the membrane. For example, signaling molecules are thought to be compartmentalized in these domains.

In one embodiment of the present invention, the method may further include heating the substrate obtained in step (ii). As the phase transition temperature of the lipids constituting a membrane varies depending on the types of lipids used to prepare a lipid layer, the substrate may be further treated by heating depending on the types of lipids used. The heating step may be carried out in accordance with conventional methods known in the art such as described in Arun Radhakrichnan and Harden McConnell, Condensed complexes in vesicles containing cholesterol and phospholipids, PANS 102, 12662-12666 2005, which is incorporated herein by reference.

The biomembrane device and the method for preparing such of the present invention include the use of a substrate to support a lipid layer.

Various substrates known in the art may be used with or without modification for the substrate of the present invention as long as it supports lipid layers of the present invention. The topographic structure may be formed directly on the substrate. Alternatively, the substrate may have a double-layered structure comprised of a lower layer of a solid support and an upper layer on which a topographic structure is formed (for example, see FIG. 2A). Further, when the lower layer of a substrate is hydrophobic, the upper layer may be prepared to have a hydrophilic nature to which a lipid layer is attached. However, when a lipid monolayer is employed on the substrate, the hydrophobic substrate may be used as it is, without treating the substrate to make it hydrophilic. When a substrate with a double-layered structure is employed, the lower and upper layers of the double-layered structure may be made of identical or different materials. Representative examples of the materials include, but are not limited to, mica, graphite, silicon dioxide, silicone and the like. The substrate prepared using said materials may include, but is not limited to, a wafer made of, for example, mica, graphite, or silicon dioxide; a polymer such as PDMS (polydimethysiloxane) or silicone; glass; and plastic. More information about the substrates may be found in the following literature [PDMS: Byron D. Gates and George M. Whitesides, Replication of vertical features smaller than 2 nm by soft lithography, J. AM. CHEM, SOC. 125, 14986-14987 2003; MICA: J. Marra and J. Israelachvili, Direct Measurements of Forces between Phosphatidylcholine and Phosphatidylethanolamine Layers in Aqueous Electrolyte Solutions, Biochemistry, 24, 4608-4618 1985; and glass quartz, silicon: L. K. Tamm and H. M. McConnell, Supported phospholipid layers, Biophys. J., 47, 105-113 1985], all of which are incorporated herein by reference. When fluorescent dyes are employed for the present invention, it is preferable to choose dyes such that the differences in the refractive index of the dyes are minimized. In one embodiment, identical dyes are used for the upper and lower layers of a substrate with a double-layered structure. In one embodiment of the present invention, as a solid support, quartz wafers with hydrophilic deposited on top are used.

The term "topographic structure" used herein indicates a topographic surface modification of a substrate. Various topographic structures of nanometer- to micrometer-scale may be employed for the present invention as long as they would be able to achieve the control of the growth, size, and distribution of lipid domains. The topographic structure may include, but is not limited to, a topographic wall, a corrugated region, and a smooth region (see FIG. 4). The topographic wall serves as a region preventing the distribution of the lipid domain, the corrugated region serves as a region prohibiting the growth of the lipid domain, and the smooth region serves as a region promoting the growth of the lipid domain. Thereby, it is possible to induce a lipid domain to grow in a predefined position within a lipid layer. For example, topographic structures as disclosed in W. M. Choi and O. O. Park, Soft-imprint technique for multilevel microstructures using poly(dimethylsiloxane) mold combined with a screen mask, Appl. Phys. Lett., 85, 3310-3312 2004; D. Braun and P. Fromherz, Fluorescence Interferometry of Neuronal Cell Adhesion on Microstructured Silicon, Phys. Rev. Lett., 81, 5241-5244 1998; Y. Zhao, C. C. Lim, D. B. Sawyer, R. Liao, X. Zhang, Microchip for subcellular mechanics study in living cells, Sensors and Actuators B, 114, 1108-1115 2006; and Y. Fua and N. K. A. Bryan, Fabrication and characterization of slanted nanopillars array, J. Vac. Sci. Technol. B, 23, 984-989 2005 may be used for the present invention, all of which are incorporated herein by reference.

According to one aspect the present invention, a topographic structure of a substrate may include at least one structure selected from the group consisting of a topographic wall, a smooth region, and a corrugated region. According to another aspect of the present invention, a topographic structure of a substrate may include a corrugated region and a smooth region. According to yet another aspect of the present invention, a topographic structure of a substrate may include a corrugated region, a smooth region, and a topographic wall formed at the interface between the corrugated region and the smooth region.

A topographic structure may be formed on a substrate by various methods known in the art in consideration of the materials constituting the substrate. The structure is formed on a substrate in such a way as to enable the attachment of a lipid layer to the substrate. For example, methods for providing a topographic structure on a substrate include, but are not limited to, etching, stamping, photo-irradiation, and deposition processes. Details for performing such methods and further methods may be found in the following literature, which are incorporated herein by reference: H. K. Taylor et al., Characterizing and Predicting Spatial Non-uniformity in the Deep Reactive Ion Etching of Silicon, J. Electrochem. Soc. 153, C575 2006; M. S. Chen et al., Structure of thin $SiO_2$ films grown on Mo 112, Phys. Rev. B 69, 155404 2004; and Jennifer S. Hovis et al., Patterning barriers to lateral diffusion in supported lipids layer membranes by blotting and stamping. Langmuir 16, 894-987 2000.

Figure 2A:
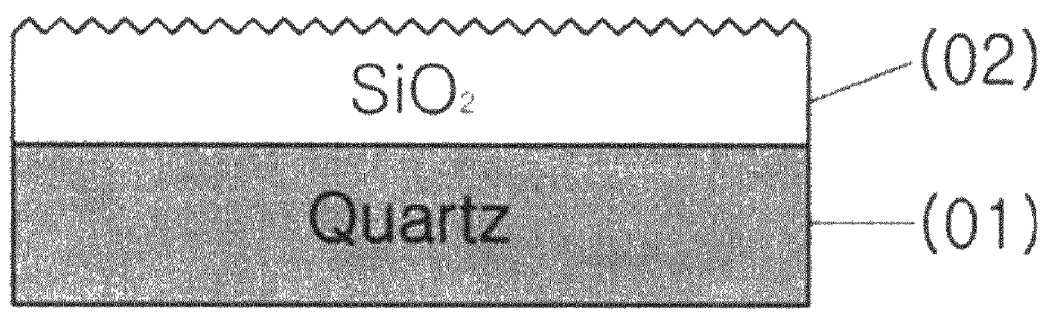
FIG. 2A is a schematic view showing a basic structure of the substrate for one embodiment of the present invention.
Figure 2B:
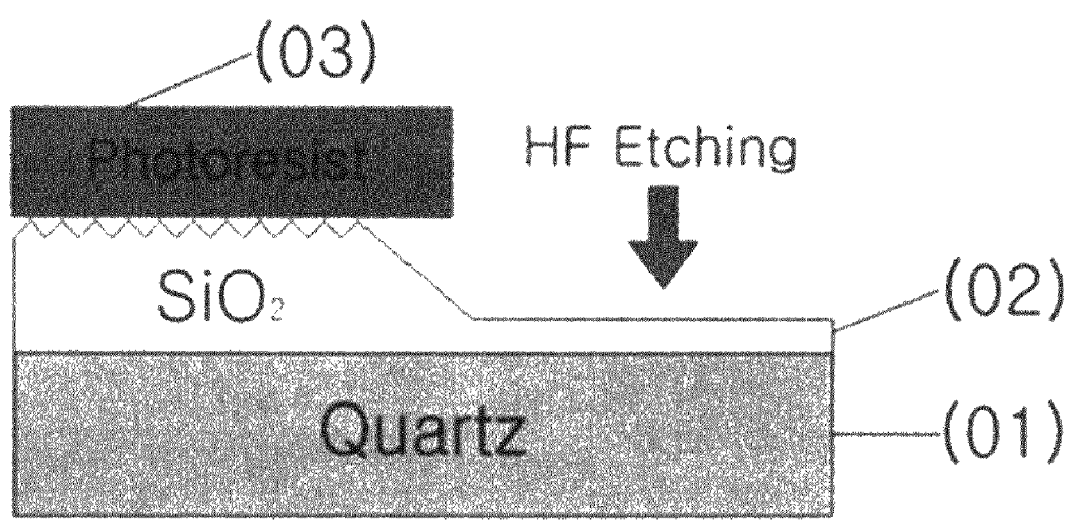
FIG. 2B is a schematic view showing a process for simultaneously providing a smooth region, a corrugated region, and a topographic wall formed at the interface between the corrugated region and the smooth region by etching.
Figure 2C:
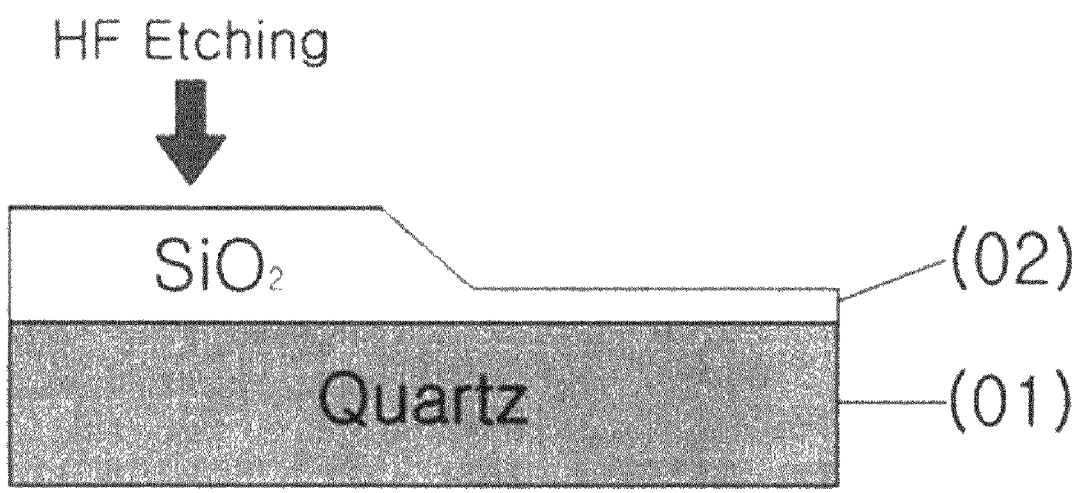
FIG. 2C is a schematic view showing a process for providing two smooth regions and a topographic wall formed at the interface between the corrugated region and the smooth region by additional etching of the substrate of FIG. 2B.
Figure 2D:
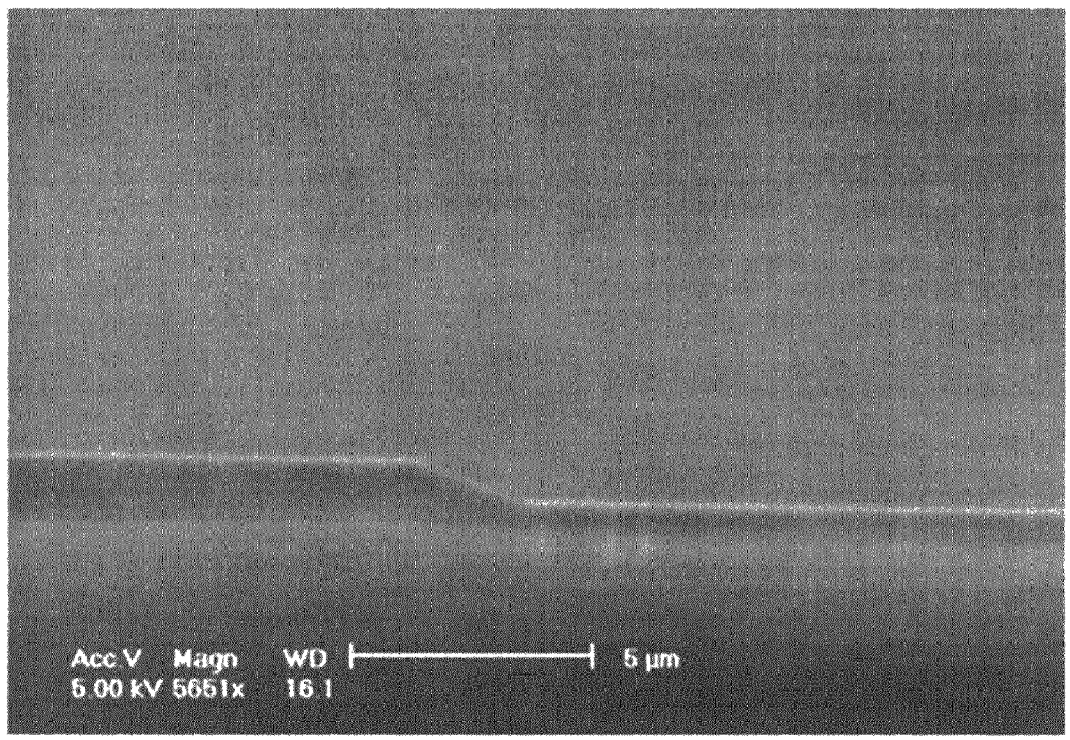
FIG. 2D is a scanning electron microscopy (SEM; XL30FEG, Philips) micrograph of the substrate of FIG. 2C.

In one embodiment of the present invention, a topographic structure may be produced on a substrate by at least one process selected from the group consisting of etching, stamping, photo-irradiation, and deposition. According to one exemplary embodiment of the present invention, as shown in FIG. 2A, a hydrophilic $SiO_2$ (02) is deposited on a quartz wafer (01) (crystal direction: 100) according to the method known in the art to provide a substrate. Then, the substrate may be further subjected to a standard photolithography process to provide a photoresist pattern 03, and the silicon oxide ($SiO_2$) layer is etched with a hydrogen fluoride (HF) as shown in FIG. 2B. Thereafter, the photoresist is removed and the substrate is etched again with hydrogen fluoride (HF) as shown in FIG. 2C to provide a substrate with a topographic structure as shown in FIG. 2D and FIG. 1.

The present inventors discovered that the topographic structure on a substrate can generate an elastic distortion in a lipid layer on the substrate, causing a difference in elastic free energy in different regions of the lipid layer, which then serves as an energy barrier to control the growth, size, and distribution of a lipid domain, for example a lipid raft. This is proven theoretically correct and practically possible by successfully preparing a biomembrane device having such characteristics (see Examples). Without wishing to be bound by theory, it is believed that the control of the growth, size, and distribution of a lipid domain by a topographic structure is possible due to the fact that the increase in the free energy per molecule of a lipid domain (e.g., a lipid raft) accompanied by the elastic distortion of a lipid domain by a topographic structure (e.g., a topographic wall) is larger than the decrease in the chemical potential per molecule accompanied by the growth of a lipid domain by several $k_B T$ (herein, $k_B$ denotes Boltzmann constant of $1.3806505 \times 10^{-23}$ J/K, T is room temperature in Kelvin unit, K. Accordingly, $k_B T$ represents energy at room temperature and thus the energy at room temperature of 20° C. (293K) will be around $4.045 \times 10^{-21}$ J. It is believed that such an increase in the free energy of a lipid domain after an elastic distortion is attributed to the high elasticity coefficient of the hydrocarbons resulting from their highly ordered structure, which is found in a lipid domain such as a lipid raft. The difference in the elastic free energy generated on a lipid layer resulting from a topographic structure formed on a substrate may be calculated by the methods known in the art, such as, for example, an effective surface roughness or a difference in the spatial frequency of the substrate, but it is not limited thereto.

In view of the foregoing, a corrugated region serves as an area prohibiting the growth of a lipid domain, a smooth region serves as an area promoting the growth of a lipid domain, and a topographic wall serves as an area preventing the distribution of a lipid domain. The control of the growth, size, and distribution of a lipid domain, such as a lipid raft, by a topographic structure includes, but is not limited to, a drift of a lipid domain to other areas of a lipid layer, a growth of a lipid domain at a predefined position in a lipid layer, localized distribution of a lipid domain, and spatial confinement of a lipid domain in a lipid layer. The fluorescent micrograph of the lipid raft region evolved over time in the lipid layer on a substrate of FIGS. 2A to 2C, as shown in FIG. 3, clearly shows that the lipid raft region is indeed produced in the smooth region and confined therein without drifting over to another area of the lipid layer across the topographic wall, while the lateral fluidity of the background lipid layer is preserved, moving freely across the topographic wall.

Figure 3:
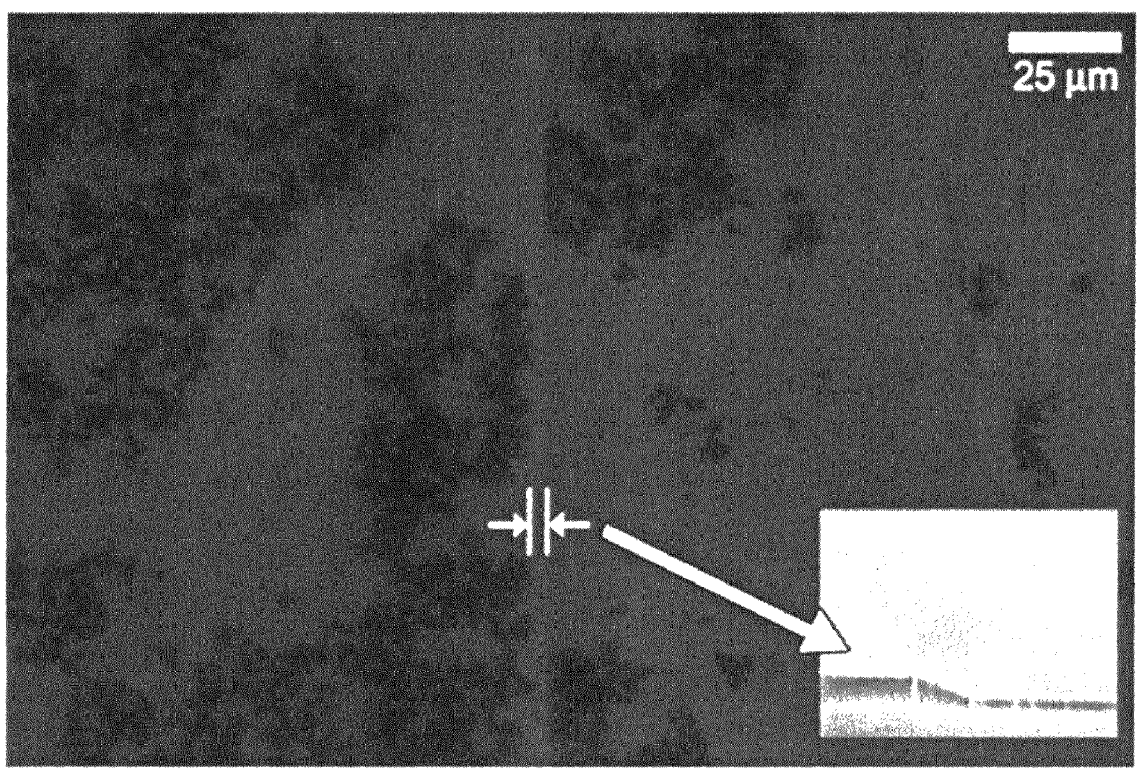
FIG. 3 is an epifluorescence microscopy (Declipse E600-POL, Nikon) micrograph of lipid raft regions formed in a lipid layer on the substrate of FIG. 2C.
Figure 4:
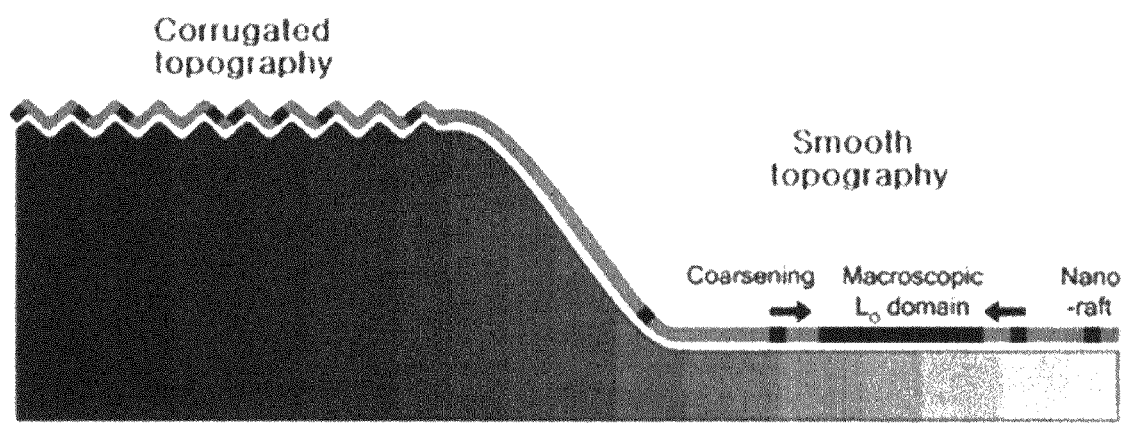
FIG. 4 is a schematic view showing the local distribution of a lipid raft within a predefined position using a topographic structure that generates an elastic energy barrier and thereby prohibits the distribution of the lipid raft to other parts of a lipid layer.

Thus, in one aspect of the present invention, the free energy barrier generated by a topographic structure not only allows the control of the drift and distribution of a lipid domain in a model biomembrane system but also enables the growth and distribution of the lipid raft in a predefined localized area in a lipid layer (see FIGS. 3 and 4). Therefore, in another aspect of the present invention, it is possible to induce a lipid raft to grow in a localized predefined area on a lipid layer by using the present methods, where the lipid rafts are formed in periodic arrays of smooth regions in a corrugated background region. The periodic arrays are also referred to as "square wells", each of which is surrounded by four topographic walls, without disrupting two dimensional continuity and fluidity of the background lipid layer (see FIGS. 6 and 7). The topographic wall at the interface of the well has a step difference of micrometer scale.

Accordingly, in another aspect, the present invention provides a method for controlling the growth, size, and distribution of a lipid domain in a lipid layer on a substrate, wherein the control is achieved by use of a substrate on which a topographic structure is provided.

The lipid raft regions produced according to embodiments of the present invention are shown to effectively capture proteins that play an important role in a signal transduction in cells, thereby rendering the crucial protein-ligand binding processes highly concentrated in the lipid raft region. This indicates that the lipid raft regions formed by the present invention function properly in vitro as they do in vivo (see Example and FIG. 7). Thus, the present methods of controlling the growth, size, and distribution of a lipid domain, and of preparing a biomembrane device, as well as a biomembrane device prepared thereby, will be useful for the study of the mechanism of the onset and development of diseases through enabling a specific/selective interaction and/or binding of proteins involved in signal transductions as well as regulation of cell functions in vitro by providing a regulated lipid domain region similar to those found in vivo. One of ordinary skill in the art would understand that the lipids constituting lipid rafts and the proteins interacting with the lipid rafts may vary depending on the specific functions the lipid rafts perform in the cells. Thus, it will be understood by one of ordinary skill in the art that the biomembrane devices of the present invention are not limited to use with only certain types of proteins and lipid rafts, but can be used with a wide variety of proteins and lipid rafts. In one embodiment of the present invention, a cholera toxin sub-unit B is shown to specifically bind to a glycolipid receptor $G_{M1}$ in the lipid raft region produced by the present method (see Example 3).

The term, "lipid layer" as used herein encompasses both a lipid mono-layer and a lipid bilayer, and thus refers to a monolayer or bilayer of lipid molecules (e.g., phospholipids) in which the lipid molecules comprised of a hydrophobic hydrocarbon chain (e.g., fatty acids) called a tail, and a hydrophilic head (e.g., phosphate), which adopt a highly ordered structure, with the tails facing each other toward the center of the layer. Examples of the lipid layer of the present invention may include any lipid layers of natural and synthetic origin, including plasma membranes found in cells and other membranous parts of cells. The representative example for the lipid molecules includes phospholipids having a phosphate head and an acyl tail.

A wide variety of lipid monolayers and bilayers derived from a natural and synthetic origin may be used for the present invention for preparing a biomembrane device and a biomembrane device prepared thereby. Further, a variety of lipid molecules from a natural and synthetic origin may be used for the preparation of the lipid layers of the present invention. When preparing lipid layers, if desired, various kinds of lipid molecules from cell membranes or synthetic origin may be used alone or in combinations in various ratios to provide a lipid domain, for example a lipid raft, of interest. One of ordinary skill in the art would appreciate that the compositions of lipids constituting cell membranes may vary depending on types and/or functions of cells in the body and that a wide variety of lipid domains other than lipid rafts are also present in cells. Therefore, one of ordinary skill in the art will clearly understand that, when preparing and using an in vitro biomembrane model system, actual compositions of the lipids that constitute the lipid layers and ratios of their individual components would vary depending on their specific needs. Accordingly, lipid components and ratios thereof to be used for the in vitro biomembrane model system may be appropriately selected by one of ordinary skill in the art depending on their specific needs. Examples of the lipids that may be used for the present invention include, but are not limited to, phosphatidylcholine (PC), phosphatidylethanolamine (PE), phosphatidylserine (PS), phosphatidylglycerol (PG), phosphatidic acid (PA), phosphatidylinositol (PI), sphingomyelin (SPM), cardiolipin, dimyristoylphosphatidic acid (DMPA), dimyristoylphosphatidylcholine (DMPC), dipalmitoylphosphatidic acid (DPPA), dioleoylphosphatidyl serine (DOPS), dimyristoylphosphatidylserine (DMPS), dipalmitoylphosphatidylserine (DPPS), dioleoylphosphatidic acid (DOPA), dioleoylphosphatidylethanolamine (DOPE), dipalmitoylphosphatidylcholine (DPPC), distearoyl phosphatidylcholine (DSPC), dioleoylphosphatidylcholine (DOPC), dipalmitoylphosphatidylglycerol (DPPG), dimyristoylphosphatidylglycerol (DMPG), dioleoylphosphatidylglycerol (DOPG), dipalmitoylphosphatidylcholine (DPPC), and the like. Furthermore, whole lipid components may be extracted from cells in accordance with the conventional methods known in the art and used as they are for the present invention without being subjected to further treatment or may be used in combination with other lipids of natural or synthetic origin in various ratios, which is within the knowledge of one of ordinary skill in the art. According to one exemplary embodiment of the present invention, a mixture of a sphingomyelin (SPM) and cholesterol as components for a lipid raft and dioleoylphosphatidylcholine (DOPC) as a component for fluid cell membranes (lipid layer) at a molar ratio of 1:1:1 are used for the present invention.

In any given situation, the lipid components to be used in the biomembrane model systems according to embodiments of the present invention may be in the form of a unilamellar or multilamellar vesicle of lipid monolayer or bilayer formed at a water-air interface. The methods for preparing such vesicles or lipid layers are known in the art, and may be found, for example, in the following publications, all of which are incorporated herein by reference: small unilamellar vesicles (SUV) (Papahadjopoulos and Miller, Biochem. Biophys. Acta., 135, 624-638 1967); reverse-phase evaporation vesicle (REV) (U.S. Pat. No. 4,235,871); stable multi-layer lamellar vesicle (SPLV) (Lenk et al., Stable Plurilamellar Vesicles, Their Preparation and Use, U.S. Pat. No. 4,522,803); and large unilamellar vesicles (Cullis et al., Extrusion Technique for Producing Unilamellar Vesicle, WO 86/00238).

Further, the lipid mono-layer or bilayer thus formed may be incorporated onto the substrate of the present invention using the methods known in the art (for example, see Cooper, M. A. Advances in Membrane Receptor Screening and Analysis, J.

Mol. Recognit. 17, 286 2004; Sackmann, E. Supported Membranes: Scientific and Practical Applications, Science, 271, 5245 1996; and Charitat, T. et al., Eur. Phys. J. B. 8, 583 1999, which are incorporated herein by reference). For example, such methods may include, but are not limited to, a rupture and fusion (vesicle fusion) method where a vesicle of monolayer or bilayer lipids having a unilamellar or multi-lamellar structure is ruptured and fused onto a hydrophilic substrate; a method where a vesicle of mono-layer or bilayer lipids having a unilamellar or multilamellar structure is fixed onto a substrate using a hydrophilic linker or a receptor with a biotinyl attached thereto; a method where whole lipids extracted from cells are fixed onto a substrate using a hydrophilic linker or a receptor with a biotinyl attached thereto; and the Langmuir-Blodgett or Langmuir-schaeffer method where mono-layer lipid layers that are formed at a water-air interface are sequentially incorporated onto a substrate.

The following examples illustrate the present invention in further detail. However, it is understood that the present invention is not limited by these examples.

EXAMPLES

Example 1

Preparing a Biomembrane Device of the Present Invention

Example 1-1

Preparation of a Substrate Having a Topographic Structure

A substrate having a topographic structure was prepared in accordance with procedures as described in Yoon T-Y et al. Topographic control of lipid raft reconstitution in model membrane, Nature Materials, 5:281-285, 2006, which is incorporated herein by reference.

In brief, hydrophilic $SiO_2$ (02) was deposited on the top of a quartz wafer (01) (crystal direction: 100) in 1.5 μm thick, as shown in FIG. 2A.

Owing to the small difference in the refractive index between $SiO_2$ and quartz (maximum difference: 0.08), the interference effect occurring as a function of the $SiO_2$ layer thickness is negligible. It is preferable to minimize the interference effect because the interference usually gives a very high background signal in the tests using fluorescent dyes. Thus, substrates to be used for the present invention need to be selected so as to minimize the interference effects.

Then, as shown in FIG. 2B, the photoresist pattern 03 was obtained by a conventional photolithography process known in the art, and then the silicon oxide ($SiO_2$) layer was etched with hydrogen fluoride (HF) to remove the photoresist. Subsequently, the entire surface was etched with hydrogen fluoride as shown in FIG. 2C to provide a smooth region and a topographic wall at the interface therebetween. FIG. 2D shows a scanning electron microscopic (SEM; XL30FEG, Philips) photograph of the thus obtained substrate having the topographic structures.

Example 1-2

Formation of a Lipid Layer on the Substrate

In order to provide a lipid layer on the substrate obtained from Example 1-1, Small Uni-lamellar Vesicles (SUVs) having a unilamellar lipid layer with a diameter of 100 nm or less were ruptured and fused on the substrate obtained from Example 1-1 as described in Yoon T-Y et al., ibid.

In brief, for producing the SUVs, sphingomyelin (SPM) and cholesterol were used as the components for a lipid raft and dioleoyl (18:1)-phosphatidylcholine (DOPC) was used as the remaining component of the lipid layer. SUVs were obtained by the following method. DOPC, SPM, and cholesterol at a molar ratio of 1:1:1 were mixed in chloroform. Then, Texas Red-dihexadecanoyl-phosphoethanolamine (Texas Red-DHPE) labeled with a red fluorescent dye was doped into the mixture at 1 mole % of the total composition. The DOPC, SPM, and cholesterol were purchased from Avanti Polar Lipids (Birmingham, Ala., USA), and the Texas Red-DHPE was purchased from Molecular Probes (Eugene, Oreg., USA). The purchased products were used without any additional purification steps. To prevent demixing of cholesterol in the mixture, the rapid solvent exchange method (Buboltz, J. T & Feigenson, G. W. A novel strategy for the preparation of liposome: rapid solvent exchange. Biochem. Biophys, Acta 1417, 232-235 (1999)) was used, in which evaporation of solvent, and desiccation and hydration processes are carried out simultaneously. The buffer used contained 100 mM of NaCl and 10 mM of Tris at pH 8.0, and hydration was performed at a concentration of 0.2 mg $ml^{-1}$. SUVs were then obtained by the extrusion method using Mini-Extruder (Avanti Polar Lipids, Birmingham, Ala.) with at least 60 filtering processes through a 50 nm filter at 50° C.

The SUVs thus prepared were allowed to rupture on the substrate, which was cleaned in a piranha solution (3:1 (v/v) $H_2SO_4$:$H_2O_2$) at 125° C. for more than 15 minutes before use, for not more than 90 seconds and to fuse onto the substrate to produce a supported lipid layer membrane (Braun, D. & Fromherz, P. Fluorescence interferometry of neuronal cell adhesion on microstructured silicon, Phys. Rev. Lett. 81, 5241-5244 (1998)). When the SUVs are ruptured and fused for a longer period of time, the obtained lipid layers will have a dense structure, which in turn is shown to inhibit the formation of a lipid raft domain. The obtained lipid layer on the substrate (supported lipid layer membrane) was stored under water to prevent exposure to air.

Example 2

Control of the Growth, Size, and Distribution of a Lipid Raft

Example 2-1

Generation of an Elastic Free Energy Barrier

The formation of a lipid raft on the substrate (supported lipid layer membrane) obtained from Example 1 was monitored.

Lipid rafts were formed by the rearrangement of a small raft in nanometer scale derived from the SUV of Example 1, which then become detectable under a fluorescent microscope.

The results are shown in FIG. 3. FIG. 3 shows a fluorescent microscopic photograph of a lipid raft, which is formed over time as described in Example 1, on the lipid layer of a substrate with a topographic structure of FIG. 2. The photograph inside of FIG. 3 shows a cross-sectional view of the substrate (supported lipid layer membrane). In FIG. 3, the lipid rafts appear darker than the background lipid layer. As shown in FIG. 3, unlike the background lipid layer which is in a fluid state, the raft region was not able to migrate beyond the curvature boundary formed by the topographic wall (indicated by the white lines in FIG. 1) and hence was confined within one area of the substrate (the left part in FIG. 3). This proves that the formation of a lipid raft region in a predefined position of interest is possible. This can be explained by the high increase in free energy of a lipid raft region resulting from a high elastic coefficient due to its highly ordered structure serving as a free energy barrier that prevents the distribution of the lipid raft.

Example 2-2

Control of the Growth, Size, and Distribution of a Lipid Raft Using a Free Energy Barrier Generated by a Topographic Structure The present inventors proved that a lipid raft region can be formed in a predefined position by the elastic free energy barrier generated by a topographic structure formed on a substrate as described previously (Yoon T-Y et al., ibid).

Figure 5A:
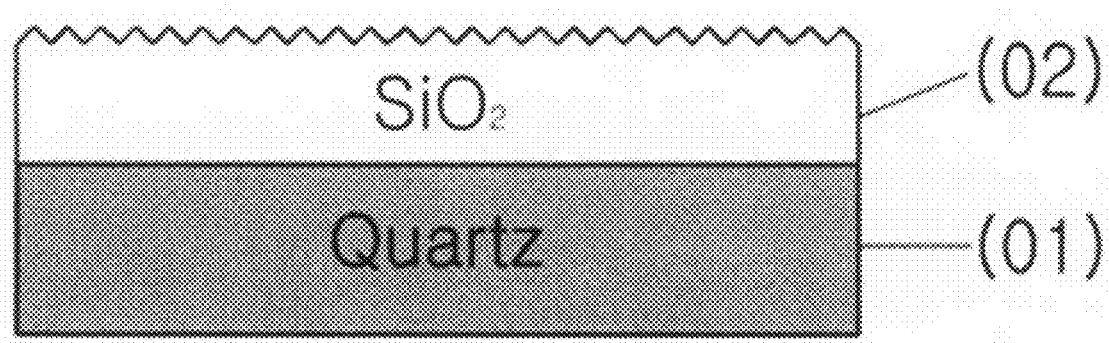
FIG. 5A is a schematic view showing a basic structure of the substrate according to one embodiment of the present invention.
Figure 5B:
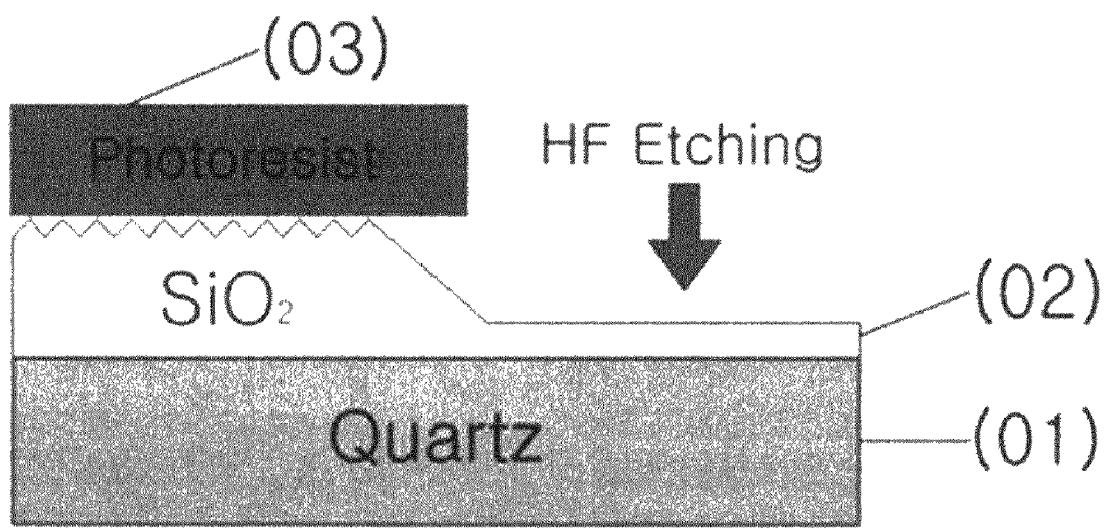
FIG. 5B is a schematic view showing a process for simultaneously providing a smooth region, a corrugated region, and a topographic wall at the interface between the corrugated region and the smooth region by etching.
Figure 5C:
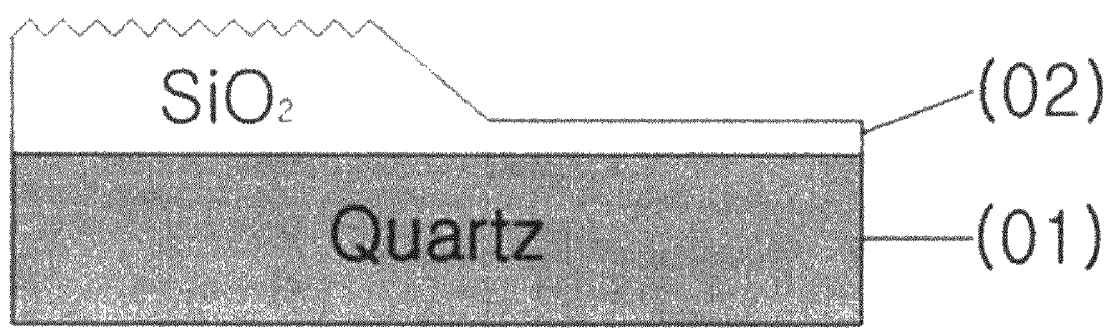
FIG. 5C is a schematic view showing a substrate with a topographic structure after the photoresist of FIG. 5B is removed.

Briefly, a smooth region, a corrugated region, and a topographic wall with a step difference of micrometer scale at the interface between the corrugated region and the smooth region were formed on the substrate (refer to FIG. 4) in accordance with the procedures as described in Example 1 and FIGS. 5A to 5C followed by the formation of a lipid layer thereon.

Figure 5D:
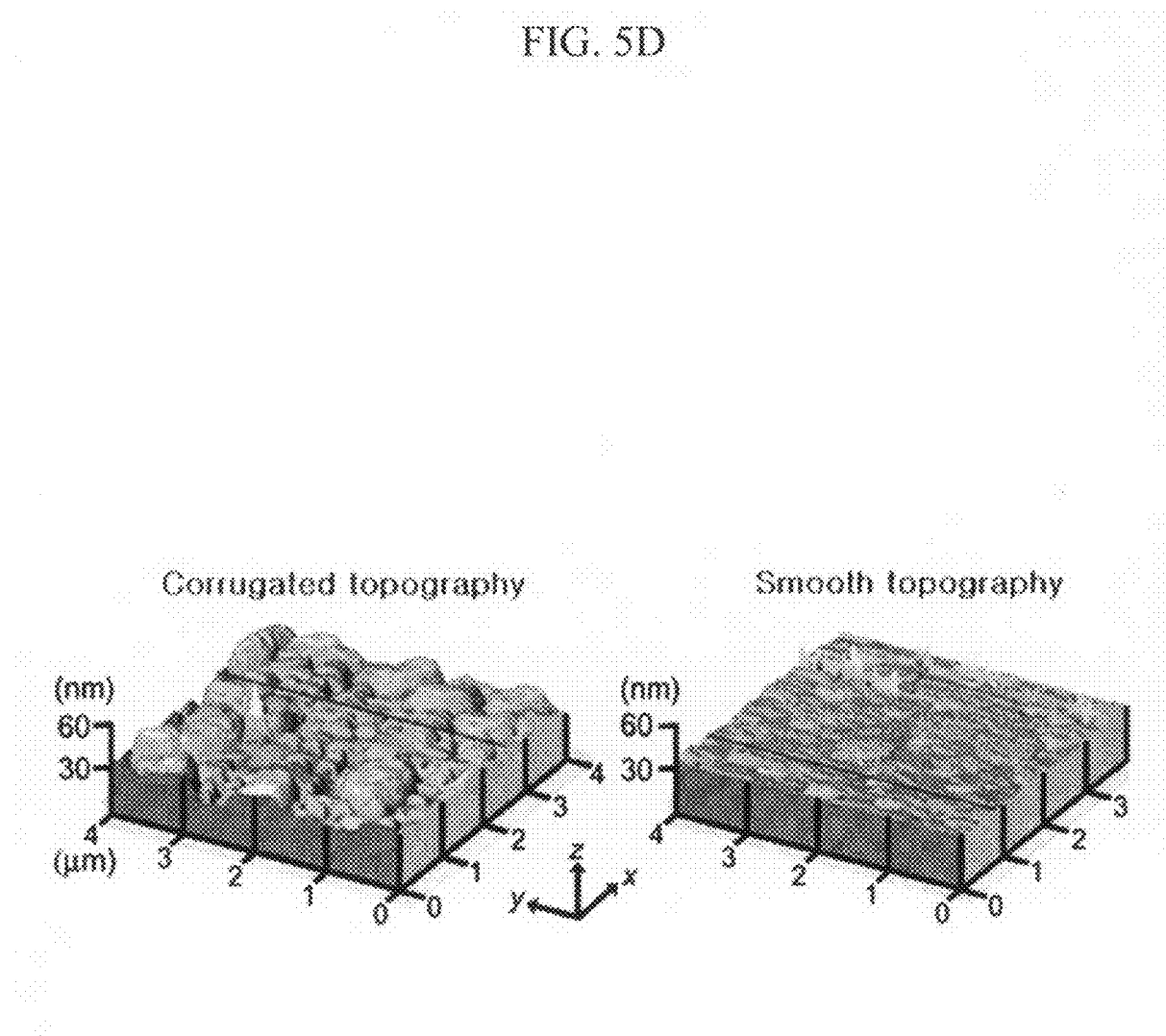
FIG. 5D is an atomic force microscopy (AFM; AutoProbe CP, Park Scientific) measurement of the corrugated region (left) and the smooth region (right) of the substrate of FIG. 5C.
Figure 5E:
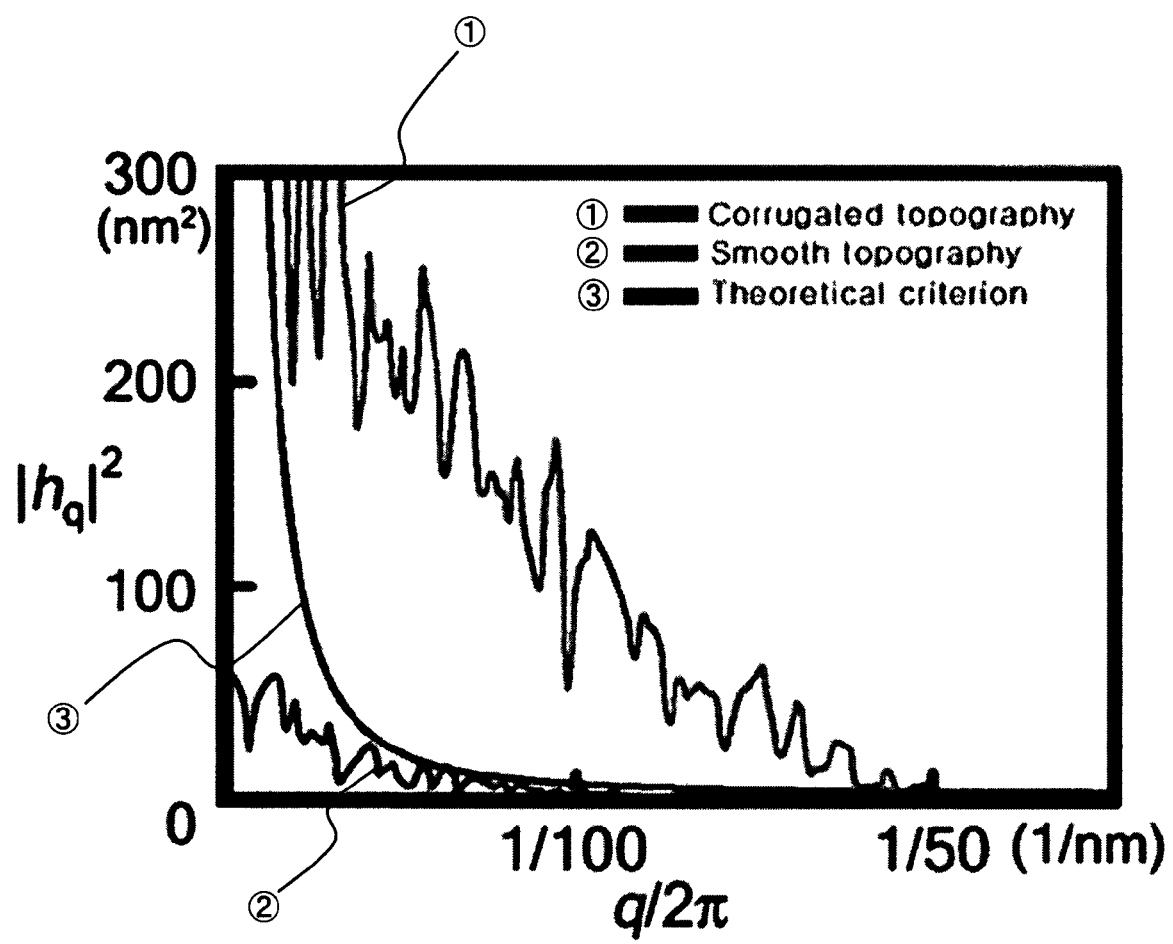
FIG. 5E is a graph showing the measurement of the magnitude of $Ih_q1^2$ of the substrate of FIG. 5C, showing the theoretical support for the selective growth of a lipid raft.

FIG. 5D shows the results of atomic force microscopy measurements of the topographic structure formed on the substrate thus produced and clearly shows the successful formation of a corrugated region (left side) and a smooth region (right side). FIG. 5E shows the results of the frequency analysis of each of the topographic structures. According to the Helfrich-type free energy, the elastic free energy barrier is represented by $$(\Delta K d^2 / 2) \sum_{\vec{q}} q^4 |h_{\vec{q}}|^2.$$

Here, $\Delta K$ denotes the difference in the rigidity coefficients between a lipid domain and the fluid phase other than the lipid domain, $|\vec{q}|=q$, AND $h_{\vec{q}}$ denotes the frequency (Fourier) component of the topographic structure.

Accordingly, it is confirmed that lipid domains are able to grow on a smooth region based on the comparison of the frequency component of the corrugated and smooth regions to the theoretical criteria that determine whether a lipid domain would grow or not.

The results provide theoretical evidence that the topographic structure can control the growth of a lipid domain in a lipid layer, in addition to the experimental evidence provided above.

In conclusion, the smooth region formed on a substrate promotes the growth of a lipid raft while the corrugated region prohibits it. The lipid raft regions once formed are not able to move freely into other parts of the lipid layer because of the high frictional resistance with the substrate as well as an elastic free energy barrier due to the topographic structure.

Example 2-3

Formation of a Lipid Raft Region at a Predefined Position

In addition to the control of the growth of a lipid raft region by controlling its distribution as in Example 2-2, the present inventors also confirmed that the formation of a lipid raft region at a predefined position is also possible by conducting the experiments as previously described (Yoon T-Y et al., ibid).

The lipid rafts were able to grow only in a certain localized area on the lipid layer that is present on periodic arrays of smooth regions in the corrugated background region, called "a square well". Each well was surrounded by four topographic walls and the lipid rafts were confined within that well structure, without distributing to outside of the well. Inside of the well is a smooth region and outside is a corrugated region and a curvature boundary formed by a topographic wall with a step difference of micrometer scale is formed therebetween.

Figure 6:
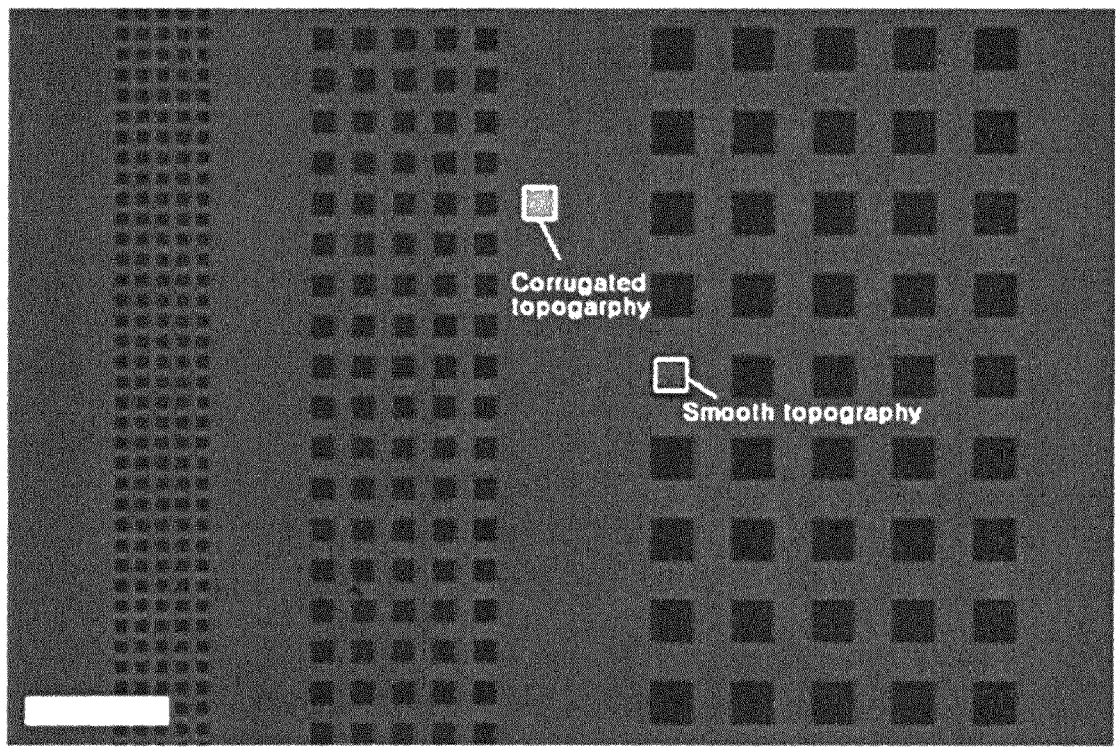
FIG. 6 is an epifluorescence micrograph of periodic arrays of smooth regions in a corrugated background region, showing the selective growth of a lipid raft in the smooth region, with a scale bar of 200 μm.

Lipid layers were then formed on the substrate having the well structures as described in Example 1 except that ganglioside (GM1, purchased from Avanti Polar Lipids) was doped to the DOPC/SPM/Cholesterol (1:1:1) at 1 mole % and were examined by a fluorescent microscope as shown in FIG. 6. GM1 serves as a receptor that binds to signal molecules as it is selectively incorporated into lipid raft regions. FIG. 6 shows that lipid rafts are formed only in the smooth region (inside of the well) and the rafts once formed remained in the smooth region blocked by the curvature boundary formed by the topographic wall resulting in no lipid raft formation outside of the well.

Example 3

Interaction Between Lipid Rafts and Membrane Proteins

Figure 7:
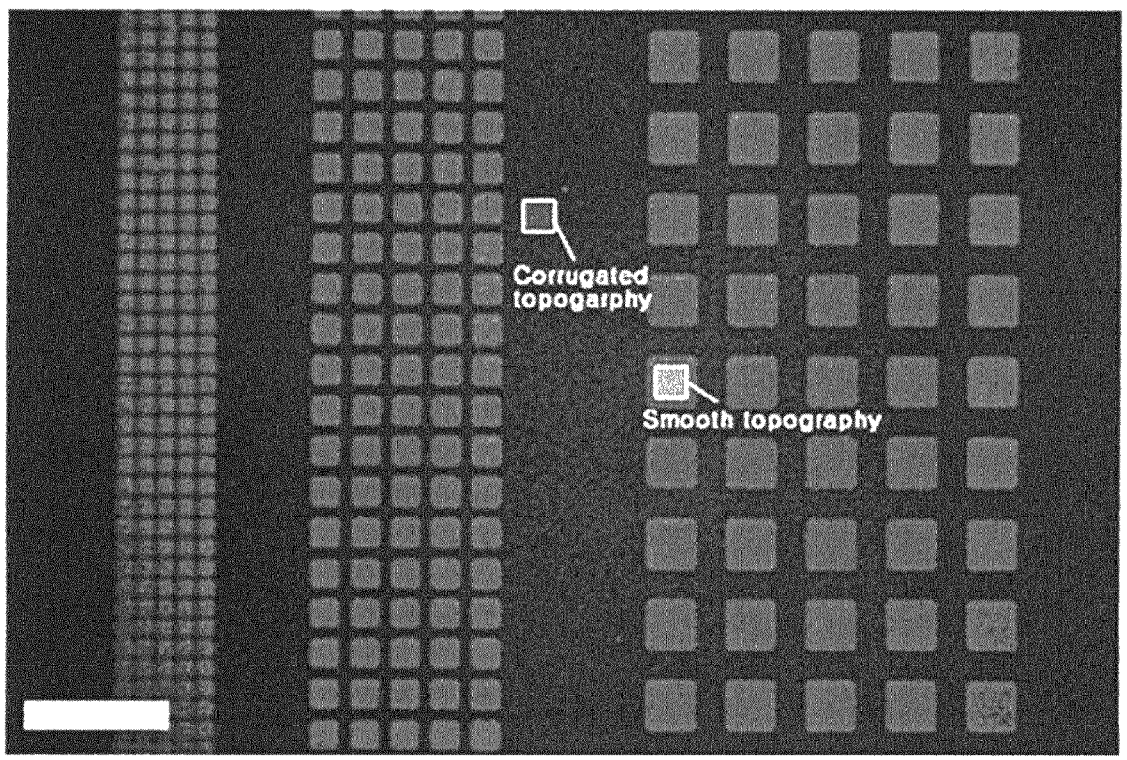
FIG. 7 is an epifluorescence micrograph showing the selective reconstitution of a Cholera toxin subunit B—glycolipid receptor $G_{M1}$ binding process in the array of FIG. 6, with a scale bar of 200 μm.

FIG. 7 shows that lipid raft domains formed inside the well structure according to Examples 2 and 3 can selectively bind to/interact with membrane proteins, indicating the reconstituted smooth regions of the present invention are indeed in liquid ordered phase and properly function as a lipid raft region as found in vivo.

Specifically, the specific binding of a cholera toxin subunit B (CTB) to a glycolipid receptor $G_{M1}$ was used as a model biochemical process. When CTB was allowed to interact with the lipid layer of the substrate, it specifically interacted with/bound to the raft region formed on the smooth region inside the square well, as shown in FIG. 7. In FIG. 7, the fluorescence in each smooth region (gray region) illustrates that CTB-GM1 binding processes are highly concentrated in these preset regions. Cholera toxins are composed of subunits A and B. The B sub-unit binds to a certain component of the lipid raft region and causes a conformational alteration of holotoxin, allowing the presentation of the A subunit to the cell surface, which is then involved in a signal transduction leading to disease development. Accordingly, the selective binding of the cholera toxin to the lipid raft region indicates that the biomembrane devices of the present invention are useful for the study of membrane proteins or the biochemical processes that are mediated by the lipid rafts, which would otherwise be very difficult to study in vitro. It further suggests that a signal transduction pathway of interest, such as that leading to the development of a certain disease, may be induced to occur only in a localized predefined area of the device.

In conclusion, the present inventors clearly showed that the control of both the equilibrium and dynamic states of lipid domains, such as lipid rafts, is possible using topographic structures formed on a substrate. Further, the magnitude of a free energy barrier generated by the topographic structure is also regulated by changing a shape of the topographic structures employed. This makes possible more precise and reliable studies on membrane proteins by the formation and control of the growth of the lipid raft in a predefined area. The biomembrane devices according to embodiments of the present invention have a wide application in a variety of areas relating to membrane protein studies involved in signal transductions as well as cell membrane studies.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method for preparing a membrane device, the method comprising:
   (i) providing a topographic structure on a substrate; and
   (ii) forming a lipid layer having a lipid domain on the topographic structure of the substrate, the topographic structure controlling a growth and a distribution of the lipid domain.

2. The method of claim 1, wherein the lipid domain is a lipid raft, and the topographic structure causes elastic distortions of the lipid layer.

3. The method of claim 1, further comprising heating the substrate on which the lipid layer is formed.

4. The method of claim 1, wherein the topographic structure of the substrate comprises at least one structure selected from the group consisting of a topographic wall prohibiting the distribution of the lipid domain, a smooth region promoting the growth of the lipid domain, and a corrugated region prohibiting the growth of the lipid domain.

5. The method of claim 1, wherein the topographic structure of the substrate comprises a corrugated region, a smooth region, and a topographic wall being formed at the interface between the corrugated region and the smooth region.

6. The method of claim 4, wherein the corrugated region prohibits the growth of a lipid domain, the smooth region promotes the growth of a lipid domain, and the topographic wall prohibits the distribution of a lipid domain.

7. The method of claim 1, wherein the control of the growth and the distribution of the lipid domain by the topographic structure includes a drift of the lipid domain in the lipid layer, the growth of the lipid domain at a predefined position in the lipid layer, a localized distribution of the lipid domain, and a spatial confinement of the lipid domain in the lipid layer.

8. The method of claim 1, wherein the substrate is a monolayer, and the topographic structure is formed directly on the substrate.

9. The method of claim 1, wherein the substrate has a double-layered structure comprising a lower layer and an upper layer on which the topographic structure is formed.

10. The method of claim 1, wherein the topographic structure is formed by at least one selected from the group consisting of etching, stamping, photo-irradiation, and deposition.

11. The method of claim 1, wherein the substrate comprises quartz wafer with hydrophilic $SiO_2$ deposited on the top of the quartz wafer.

12. The method of claim 11, wherein the providing of the topographic structure on the substrate comprises applying a patterned photoresist over $SiO_2$, exposing the photoresist to a pattern of light, and etching the region which is not protected by the photoresist.

13. The method of claim 12, wherein the providing of the topographic structure further comprises removing the photoresist and etching the region which is not etched.

14. The method of claim 1, wherein the lipid layer comprises dioleoylphosphatidylcholine and the lipid domain including a mixture of sphingomyelin and cholesterol, and the ratio of the dioleoylphosphatidylcholine, the sphingomyelin and the cholesterol is 1:1:1, and the topographic structure causes elastic distortions of the lipid layer.

15. The method of claim 1, wherein the lipid layer is formed by at least one process selected from the group consisting of (i) rupture and fusion of a vesicle on the substrate, (ii) fixation of a vesicle onto the substrate by using a hydrophilic linker or a receptor with a biotinyl attached thereto, (iii) fixation of whole lipids extracted from cells onto the substrate by using a hydrophilic linker or a receptor with a biotinyl attached thereto, and (iv) incorporating a lipid mono-layer formed on a water-air interface onto the substrate.

16. The method of claim 1, wherein the substrate is prepared using material selected from the group consisting of mica, graphite, silicon dioxide, polydimethylsiloxane, silicone, glass, and plastic.

17. The method of claim 1, further comprising employing fluorescent dyes to the membrane device.

18. The method of claim 1, wherein the lipid layer is comprised of phospholipid.

19. A method for controlling a formation of a lipid domain in a lipid layer on a substrate, comprising using at least two topographic structures formed on the substrate to control a growth, a size and a distribution of the lipid domain by elastic distortions of the lipid layer caused by said at least two topographic structures.

20. The method of claim 19, wherein the use of said at least two topographic structures comprise forming at least two of (i) a topographic wall prohibiting the distribution of the lipid domain, (ii) a smooth region promoting the growth of the lipid domain, and (iii) a corrugated region prohibiting the growth of the lipid domain to control the formation of the lipid domain.

21. The method of claim 19, wherein the lipid domain is a lipid raft.

22. The method of claim 19, wherein the control of the growth and the distribution of the lipid domain includes a drift of the lipid domain in the lipid layer, a growth of the lipid domain at a predefined position in the lipid layer, and a localized distribution of the lipid domain and a spatial confinement of the lipid domain.

23. The method of claim 19, wherein the topographic structures are formed by at least one selected from the group consisting of etching, stamping, photo-irradiation, and deposition.

24. The method of claim 19, wherein the lipid layer is formed by at least one process selected from the group consisting of (i) rupture and fusion of a vesicle on the substrate, (ii) fixation of a vesicle onto the substrate by using a hydrophilic linker or a receptor with a biotinyl attached thereto, (iii) fixation of whole lipids extracted from cells onto the substrate by using a hydrophilic linker or a receptor with a biotinyl attached thereto, and (iv) incorporating a lipid mono-layer formed on a water-air interface onto the substrate.

25. The method of claim 19, wherein the substrate is prepared using material selected from the group consisting of mica, graphite, silicon dioxide, polydimethylsiloxane silicone, glass, and plastic.

* * * * *